(12) United States Patent
Aoki et al.

(10) Patent No.: US 12,390,127 B2
(45) Date of Patent: Aug. 19, 2025

(54) MUSCLE ACTIVITY OUTPUT SYSTEM

(71) Applicant: TOYOTA JIDOSHA KABUSHIKI KAISHA, Toyota (JP)

(72) Inventors: Eisuke Aoki, Toyota (JP); Yuko Nakahira, Nagakute (JP); Daisuke Yamada, Nagakute (JP); Hidekazu Nishigaki, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 272 days.

(21) Appl. No.: 17/965,068

(22) Filed: Oct. 13, 2022

(65) Prior Publication Data

US 2023/0148907 A1    May 18, 2023

(30) Foreign Application Priority Data

Nov. 12, 2021 (JP) .................. 2021-184939

(51) Int. Cl.
*A61B 5/11* (2006.01)
*A63B 22/06* (2006.01)

(52) U.S. Cl.
CPC ........ *A61B 5/1107* (2013.01); *A63B 22/0605* (2013.01); *A63B 2208/0233* (2013.01)

(58) Field of Classification Search
CPC . A61B 5/1107; A61B 5/1116; A61B 2505/09; A63B 22/0605; A63B 2208/0233; A63B 22/0694; A63B 22/0023; A63B 22/04; A63B 22/0664; A63B 22/205; A63B 23/12; A63B 24/0062; A63B 2022/0688

See application file for complete search history.

(56) References Cited

U.S. PATENT DOCUMENTS

| | | | |
|---|---|---|---|
| 11,883,712 B2 * | 1/2024 | Aoki | A63B 21/0552 |
| 12,005,305 B2 * | 6/2024 | Takeda | A63B 22/0694 |
| 2011/0105962 A1 | 5/2011 | Ochi et al. | |
| 2016/0023081 A1 * | 1/2016 | Popa-Simil | B62J 45/412 700/91 |
| 2017/0136299 A1 | 5/2017 | Bounyong et al. | |

(Continued)

FOREIGN PATENT DOCUMENTS

| | | | | |
|---|---|---|---|---|
| CN | 205549366 U | * | 9/2016 | ........... A61H 9/0085 |
| CN | 107982026 A | * | 5/2018 | ........... A61H 1/0237 |

(Continued)

*Primary Examiner* — Octavia Hollington
(74) *Attorney, Agent, or Firm* — Oliff PLC

(57) ABSTRACT

A muscle activity output system includes: a muscle activity database configured to hold movable part attitude information and muscle activity information in such a manner that the movable part attitude information and the muscle activity information are linked to each other; and a processor. The movable part attitude information indicates an attitude of a movable part of training equipment. The muscle activity information indicates a muscle activity of each of muscle sites of the exerciser. The processor is configured to acquire the movable part attitude information while the exerciser is moving the body along the trajectory, acquire current muscle activity information for each of the muscle sites based on current movable part attitude information of the training equipment and the muscle activity database, and output the current muscle activity information for each of the muscle sites.

6 Claims, 11 Drawing Sheets

(56) References Cited

U.S. PATENT DOCUMENTS

| | | | | |
|---|---|---|---|---|
| 2018/0126220 A1* | 5/2018 | Palmer | ............... | A63B 22/0694 |
| 2020/0016453 A1* | 1/2020 | Kollreider | .......... | A63B 24/0087 |
| 2023/0146049 A1* | 5/2023 | Aoki | .................. | A63B 22/0694 |
| | | | | 482/7 |
| 2023/0149776 A1* | 5/2023 | Aoki | .................. | A63B 24/0062 |
| | | | | 482/8 |
| 2023/0149777 A1* | 5/2023 | Aoki | .................. | A63B 24/0087 |
| | | | | 482/5 |
| 2024/0139583 A1* | 5/2024 | Aoki | .................. | A63B 21/1609 |

FOREIGN PATENT DOCUMENTS

| | | | | | |
|---|---|---|---|---|---|
| CN | 109157233 | A | | 1/2019 | |
| GB | 2371997 | A | * | 8/2002 | ........... A63B 22/001 |
| JP | H1094577 | A | | 4/1998 | |
| JP | 2003116822 | A | * | 4/2003 | |
| JP | 2017-094054 | A | | 6/2017 | |
| KR | 20200084669 | A | * | 7/2020 | |

\* cited by examiner

FIG. 5

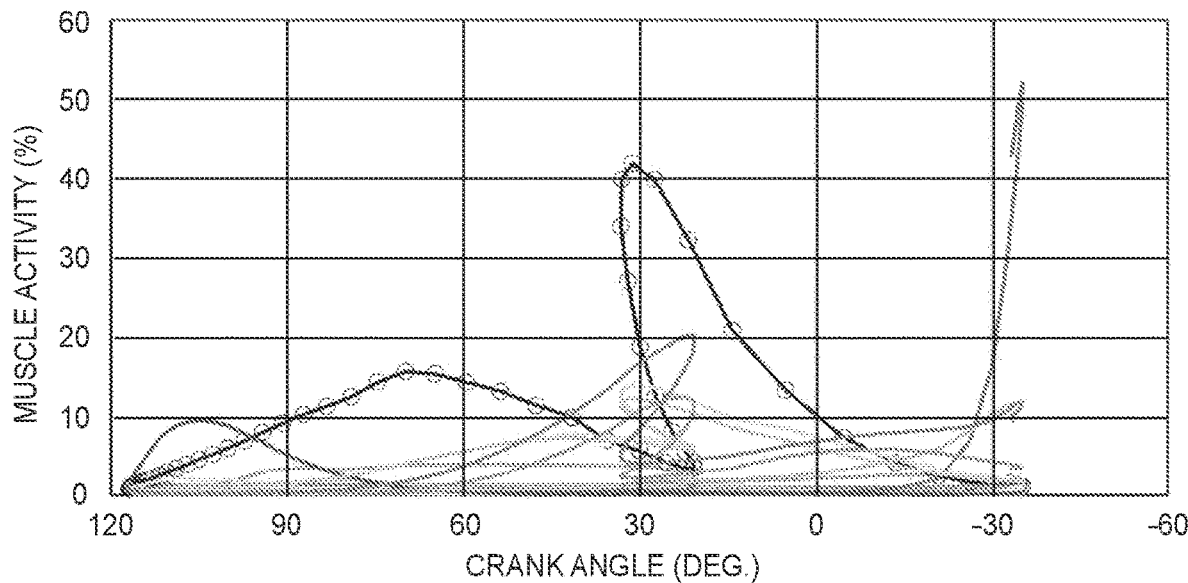

MUSCLE ACTIVITIES OF RIGHT SIDE OF BODY

- RECTUS ABDOMINIS (TRUNK: LEAN FORWARD) RIGHT
- RECTUS FEMORIS (HIP: FLEXED, KNEE: EXTENDED) RIGHT
- SOLEUS (FOOT: PLANTARFLEXED, DEEP MUSCLE) RIGHT
- PSOAS MAJOR (HIP: FLEXED, DEEP MUSCLE) RIGHT
- VASTUS MEDIALIS (KNEE: EXTENDED) RIGHT
- GLUTEUS MEDIUS (HIP: ABDUCTED, DEEP MUSCLE) RIGHT
- ILIACUS (HIP: FLEXED, DEEP MUSCLE) RIGHT
- OBTURATOR EXTERNUS (HIP: LATERALLY ROTATED, DEEP MUSCLE) RIGHT
- ADDUCTOR BREVIS (HIP: ADDUCTED, DEEP MUSCLE) RIGHT
- POPLITEUS (KNEE: FLEXED, DEEP MUSCLE) RIGHT
- ERECTOR SPINAE (TRUNK: LEANED BACKWARD) RIGHT
- BICEPS FEMORIS (HIP: EXTENDED, KNEE: FLEXED) RIGHT
- TIBIALIS ANTERIOR (FOOT: DORSIFLEXED) RIGHT
- GLUTEUS MAXIMUS (HIP: EXTENDED) RIGHT
- GASTROCNEMIUS (KNEE: FLEXED, FOOT: PLANTARFLEXED) RIGHT
- GLUTEUS MINIMUS (HIP: ABDUCTED, DEEP MUSCLE) RIGHT
- QUADRATUS FEMORIS (HIP: LATERALLY ROTATED, DEEP MUSCLE) RIGHT
- VASTUS INTERMEDIUS (KNEE: EXTENDED, DEEP MUSCLE) RIGHT
- PLANTARIS (FOOT: PLANTARFLEXED, DEEP MUSCLE) RIGHT
- PSOAS MAJOR (HIP: FLEXED, DEEP MUSCLE) RIGHT

FIG. 6

| Data No. | HEIGHT | CRANK ROTATIONAL SPEED | CRANK LOAD AMOUNT | CRANK ROTATIONAL DIRECTION | EXERCISE CONDITION 4 | . | . | EXERCISE CONDITION 15 | EXERCISE CONDITION 16 | CORRESPONDENCE INFORMATION |
|---|---|---|---|---|---|---|---|---|---|---|
| 1 | 145 | 30 | 0.1 | FORWARD | . | . | . | . | . | [................] |
| 2 | 145 | 30 | 0.1 | FORWARD | . | . | . | . | . | [................] |
| . | . | . | . | . | . | . | . | . | . | [................] |
| . | . | . | . | . | . | . | . | . | . | [................] |
| 99999 | 145 | 30 | 1.5 | REVERSE | . | . | . | . | . | [................] |
| 100000 | 145 | 30 | 1.5 | REVERSE | . | . | . | . | . | [................] |
| 100001 | 145 | 40 | 0.1 | FORWARD | . | . | . | . | . | [................] |
| 100002 | 145 | 40 | 0.1 | FORWARD | . | . | . | . | . | [................] |
| . | . | . | . | . | . | . | . | . | . | [................] |
| . | . | . | . | . | . | . | . | . | . | [................] |
| 199999 | 145 | 40 | 1.5 | REVERSE | . | . | . | . | . | [................] |
| 200000 | 145 | 40 | 1.5 | REVERSE | . | . | . | . | . | [................] |
| 200001 | 145 | 50 | 0.1 | FORWARD | . | . | . | . | . | [................] |
| 200002 | 145 | 50 | 0.1 | FORWARD | . | . | . | . | . | [................] |
| . | . | . | . | . | . | . | . | . | . | [................] |
| . | . | . | . | . | . | . | . | . | . | [................] |
| 299999 | 145 | 50 | 1.5 | REVERSE | . | . | . | . | . | [................] |
| 300000 | 145 | 50 | 1.5 | REVERSE | . | . | . | . | . | [................] |
| 300001 | 145 | 60 | 0.1 | FORWARD | . | . | . | . | . | [................] |
| 300002 | 145 | 60 | 0.1 | FORWARD | . | . | . | . | . | [................] |
| . | . | . | . | . | . | . | . | . | . | [................] |
| . | . | . | . | . | . | . | . | . | . | [................] |
| 399999 | 145 | 60 | 1.5 | REVERSE | . | . | . | . | . | [................] |
| 400000 | 145 | 60 | 1.5 | REVERSE | . | . | . | . | . | [................] |
| 400001 | 150 | . | . | . | . | . | . | . | . | [................] |
| 400002 | . | . | . | . | . | . | . | . | . | [................] |
| . | . | . | . | . | . | . | . | . | . | [................] |
| 800001 | 155 | . | . | . | . | . | . | . | . | [................] |
| . | . | . | . | . | . | . | . | . | . | [................] |
| . | . | . | . | . | . | . | . | . | . | [................] |
| 1200001 | 160 | . | . | . | . | . | . | . | . | [................] |
| . | . | . | . | . | . | . | . | . | . | [................] |
| . | . | . | . | . | . | . | . | . | . | [................] |
| 1600001 | 165 | . | . | . | . | . | . | . | . | [................] |
| . | . | . | . | . | . | . | . | . | . | [................] |
| . | . | . | . | . | . | . | . | . | . | [................] |

FIG. 7

| BODY-SPECIFIC INFORMATION | 202a |
|---|---|
| YOUR HEIGHT? | 160 cm |

| EXERCISE CONDITIONS | 202b |
|---|---|
| CRANK ROTATIONAL SPEED? | 30 rpm |
| CRANK LOAD AMOUNT? | 0.1 Nm |
| CRANK ROTATIONAL DIRECTION? | FORWARD |

MUSCLE ACTIVITIES — 202c

MUSCLE ACTIVITY OUTPUT SYSTEM

CROSS-REFERENCE TO RELATED APPLICATION

This application claims priority to Japanese Patent Application No. 2021-184939 filed on Nov. 12, 2021, incorporated herein by reference in its entirety.

BACKGROUND

1. Technical Field

The present disclosure relates to muscle activity output systems, muscle activity output methods, and non-transitory storage media.

2. Description of Related Art

Japanese Unexamined Patent Application Publication No. 10-94577 (JP 10-94577 A) discloses a pedal exercise device that is used in a sitting position.

SUMMARY

Surface electromyography sensors that measure a myopotential that is an action potential generated during contractile activity of muscle fibers are known in the art. By attaching a surface electromyography sensor to the skin closest to a muscle site to be monitored, the muscle activity of this muscle site can be monitored.

However, monitoring of the muscle activity using a surface electromyography sensor has the following problems. A surface electromyography sensor can monitor only the muscle site of the part to which it is attached. Therefore, when it is desired to monitor the muscle activities of a large number of muscle sites simultaneously, a large number of surface electromyography sensors need to be attached to desired parts each time. This is very troublesome.

A surface electromyography sensor can also only monitor the muscle activity of a surface muscle. A needle electrode is required to monitor the muscle activity of a deep muscle. However, needle electrodes cannot be used during exercise.

The present disclosure provides a technique of being aware of a current muscle activity of each muscle site including deep muscles.

A muscle activity output system according to a first aspect of the present disclosure includes: a muscle activity database configured to hold movable part attitude information and muscle activity information in such a manner that the movable part attitude information and the muscle activity information are linked to each other; and a processor. The movable part attitude information indicates an attitude of a movable part of training equipment when an exerciser moves a body of the exerciser along a trajectory defined by the training equipment. The muscle activity information indicates a muscle activity of each of muscle sites of the exerciser. The training equipment being equipment that applies a load to muscles of the exerciser. The processor is configured to acquire the movable part attitude information while the exerciser is moving the body along the trajectory. The processor is configured to acquire current muscle activity information for each of the muscle sites based on current movable part attitude information of the training equipment and the muscle activity database. The processor is configured to output the current muscle activity information for each of the muscle sites.

With the above configuration, it is possible to be aware of the current muscle activity of each of the muscle sites including deep muscles. It is therefore possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved. Moreover, presenting muscles being activated on an exercising human body model to the exerciser allows the exerciser to exercise while paying attention to those muscles. Therefore, the exercise effect can be expected to be enhanced.

In the muscle activity output system according to the first aspect of the present disclosure, the training equipment may be a pedal exercise device with which the exerciser performs a pedaling exercise while being in a sitting position. The movable part attitude information of the training equipment may be crank angle information indicating a crank angle of the pedal exercise device.

In the muscle activity output system according to the first aspect of the present disclosure, the muscle activity database may be configured to hold the movable part attitude information and the muscle activity information in such a manner that the movable part attitude information and the muscle activity information are linked to exercise condition information indicating an exercise condition of the exerciser. The processor may be configured to acquire the exercise condition information. The processor may be configured to acquire the current muscle activity information for each of the muscle sites based on the current movable part attitude information of the training equipment, the exercise condition information, and the muscle activity database. With the above configuration, it is possible to be accurately aware of the current muscle activity of each of the muscle sites including deep muscles.

In the muscle activity output system according to the first aspect of the present disclosure, the muscle activity database may be configured to hold the movable part attitude information and the muscle activity information in such a manner that the movable part attitude information and the muscle activity information are linked to body-specific information of the exerciser. The processor may be configured to acquire the body-specific information. The processor may be configured to acquire the current muscle activity information for each of the muscle sites based on the current movable part attitude information of the training equipment, the body-specific information, and the muscle activity database. With the above configuration, it is possible to be accurately aware of the current muscle activity of each of the muscle sites including deep muscles.

In the muscle activity output system according to the first aspect of the present disclosure, the muscle activity information may indicate muscle activities of deep muscles of the exerciser.

A muscle activity output method according to a second aspect of the present disclosure includes: acquiring movable part attitude information while an exerciser is moving a body of the exerciser along a trajectory defined by training equipment that applies a load to muscles of the exerciser; acquiring current muscle activity information for each of muscle sites based on current movable part attitude information of the training equipment and a muscle activity database; and outputting the current muscle activity information for each of the muscle sites. The movable part attitude information indicates an attitude of a movable part of the training equipment when the exerciser moves the body along the trajectory. The muscle activity database is configured to hold the movable part attitude information and the muscle activity information in such a manner that the movable part attitude information and the muscle activity information are linked to each other. The muscle activity information indicates a muscle activity of each of the muscle sites of the exerciser.

With the above method, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

A non-transitory storage medium according to a third aspect of the present disclosure stores instructions that are executable by one or more processors and that cause the one or more processors to perform functions. The functions include: acquiring movable part attitude information while an exerciser is moving a body of the exerciser along a trajectory defined by training equipment that applies a load to muscles of the exerciser; acquiring current muscle activity information for each of muscle sites based on current movable part attitude information of the training equipment and a muscle activity database; and outputting the current muscle activity information for each of the muscle sites. The movable part attitude information indicates an attitude of a movable part of the training equipment when the exerciser moves the body along the trajectory. The muscle activity database is configured to hold the movable part attitude information and the muscle activity information in such a manner that the movable part attitude information and the muscle activity information are linked to each other. The muscle activity information indicates a muscle activity of each of the muscle sites of the exerciser.

With the above non-transitory storage medium, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

A muscle activity output system according to a fourth aspect of the present disclosure includes: a muscle activity database configured to hold movable part attitude information and muscle activity information in such a manner that the movable part attitude information and the muscle activity information are linked to each other; and a processor. The movable part attitude information indicates an attitude of a movable part of training equipment when an exerciser moves a body of the exerciser along a trajectory defined by the training equipment. The muscle activity information indicates a muscle activity of each of muscle sites of the exerciser. The training equipment is equipment that applies a load to muscles of the exerciser. The processor is configured to acquire body posture information of the exerciser while the exerciser is moving the body along the trajectory. The processor is configured to convert the body posture information to the movable part attitude information. The processor is configured to acquire current muscle activity information for each of the muscle sites based on current movable part attitude information of the training equipment and the muscle activity database. The processor is configured to output the current muscle activity information for each of the muscle sites.

With the above configuration, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

A muscle activity output method according to a fifth aspect of the present disclosure includes: acquiring body posture information of an exerciser while the exerciser is moving a body of the exerciser along a trajectory defined by training equipment that applies a load to muscles of the exerciser; converting the body posture information to movable part attitude information; acquiring current muscle activity information for each of muscle sites based on current movable part attitude information of the training equipment and a muscle activity database; and outputting the current muscle activity information for each of the muscle sites. The movable part attitude information indicates an attitude of a movable part of the training equipment when the exerciser moves the body along the trajectory. The muscle activity database is configured to hold the movable part attitude information and the muscle activity information in such a manner that the movable part attitude information and the muscle activity information are linked to each other. The muscle activity information indicates a muscle activity of each of the muscle sites of the exerciser.

With the above method, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

A non-transitory storage medium according to a sixth aspect of the present disclosure stores instructions that are executable by one or more processors and that cause the one or more processors to perform functions. The functions include: acquiring body posture information of an exerciser while the exerciser is moving a body of the exerciser along a trajectory defined by training equipment that applies a load to muscles of the exerciser; converting the body posture information to movable part attitude information; acquiring current muscle activity information for each of muscle sites based on current movable part attitude information of the training equipment and a muscle activity database; and outputting the current muscle activity information for each of the muscle sites. The movable part attitude information indicates an attitude of a movable part of the training equipment when the exerciser moves the body along the trajectory. The muscle activity database is configured to hold the movable part attitude information and the muscle activity information in such a manner that the movable part attitude information and the muscle activity information are linked to each other. The muscle activity information indicates a muscle activity of each of the muscle sites of the exerciser.

With the above non-transitory storage medium, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

A muscle activity output system according to a seventh aspect of the present disclosure includes: a muscle activity database configured to hold body posture information and muscle activity information in such a manner that the body posture information and the muscle activity information are linked to each other; and a processor. The body posture information indicates a body posture of an exerciser when the exerciser moves a body of the exerciser along a predetermined trajectory. The muscle activity information indicates a muscle activity of each of muscle sites of the exerciser. The processor is configured to acquire the body posture information while the exerciser is moving the body along the trajectory. The processor is configured to acquire current muscle activity information for each of the muscle sites based on current body posture information of the exerciser and the muscle activity database. The processor is configured to output the current muscle activity information for each of the muscle sites.

In the muscle activity output system according to the seventh aspect of the present disclosure, the body posture of the exerciser may include a joint angle of a joint of the body of the exerciser.

In the muscle activity output system according to the seventh aspect of the present disclosure, the muscle activity information may indicate muscle activities of deep muscles of the exerciser.

A muscle activity output method according to an eighth aspect of the present disclosure includes: acquiring body posture information while an exerciser is moving a body of the exerciser along a predetermined trajectory; acquiring current muscle activity information for each of muscle sites based on current body posture information of the exerciser and a muscle activity database; and outputting the current muscle activity information for each of the muscle sites. The body posture information indicates a body posture of the exerciser when the exerciser moves the body along the predetermined trajectory. The muscle activity database is configured to hold the body posture information and muscle activity information in such a manner that the body posture information and the muscle activity information are linked to each other. The muscle activity information indicates a muscle activity of each of the muscle sites of the exerciser.

With the above method, since it is possible to be aware of the current muscle activity of each of the muscle sites including deep muscles, it is possible to check whether muscle sites to be activated have been activated and muscle sites not to be activated have not been activated. Accordingly, the exerciser can check whether an exercise the exerciser is performing is an exercise that suits his or her purpose. As a result, an effective exercise is achieved.

A non-transitory storage medium according to a ninth aspect of the present disclosure stores instructions that are executable by one or more processors and that cause the one or more processors to perform functions. The functions include: acquiring body posture information while an exerciser is moving a body of the exerciser along a predetermined trajectory; acquiring current muscle activity information for each of muscle sites based on current body posture information of the exerciser and a muscle activity database; and outputting the current muscle activity information for each of the muscle sites. The body posture information indicates a body posture of the exerciser when the exerciser moves the body along the predetermined trajectory. The muscle activity database is configured to hold the body posture information and muscle activity information in such a manner that the body posture information and the muscle activity information are linked to each other. The muscle activity information indicates a muscle activity of each of the muscle sites of the exerciser.

According to the above non-transitory storage medium, since it is possible to be aware of the current muscle activity of each of the muscle sites including deep muscles, it is possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved.

According to the above configuration, it is possible to be aware of the current muscle activity of each of the muscle sites including deep muscles. It is therefore possible to check whether muscle sites to be activated have been activated and muscle sites not to be activated have not been activated. Accordingly, it is possible to check whether an exercise the exerciser is performing is an exercise that suits his or her purpose. As a result, an effective exercise is achieved. Moreover, presenting muscles being activated on an exercising human body model to the exerciser allows the exerciser to exercise while paying attention to those muscles. Therefore, the exercise effect can be expected to be enhanced.

BRIEF DESCRIPTION OF THE DRAWINGS

Features, advantages, and technical and industrial significance of exemplary embodiments of the present disclosure will be described below with reference to the accompanying drawings, in which like signs denote like elements, and wherein:

FIG. 5 illustrates the relationship between the crank angle and the muscle activity (first embodiment);

FIG. 6 shows the structure of a muscle activity database (first embodiment);

FIG. 7 shows a display example of a touch panel display (first embodiment);

DETAILED DESCRIPTION OF EMBODIMENTS

Hereinafter, the present disclosure will be described based on first to third embodiments. The disclosure in the claims is not limited to the following embodiments. Not all of the configurations described in the embodiments are essential as means for solving the problems. For the sake of clarity, omission and simplification are made in the following description and drawings as appropriate. The same elements are denoted by the same reference signs throughout the drawings, and duplicate descriptions will be omitted as necessary.

First Embodiment

A first embodiment of the present disclosure will be described with reference to FIGS. 1 to 8. In the first embodiment, a pedal exercise device will be described as an example of training equipment. The training equipment is a pedal exercise device (hereinafter sometimes simply referred to as the "exercise device") for an exerciser to perform a pedaling exercise. A muscle activity output system and muscle activity output method according to the present embodiment perform a process of outputting current muscle activity information of each muscle site including deep muscles during training with the pedal exercise device. The muscle activity output system and the muscle activity output method output, for example, current muscle activity information of each muscle site to an exerciser who performs a pedaling exercise or an assistant who assists the exerciser in the pedaling exercise via a display. The exerciser or the assistant can thus be aware of the current muscle activity of each muscle site including deep muscles. The exerciser or the assistant can therefore check whether muscle sites to be activated have been activated and muscle sites not to be activated have not been activated. Accordingly, the exerciser or the assistant can check whether the exercise the exerciser is performing is an exercise that suits the exerciser's purpose. As a result, an effective exercise is achieved. Moreover, presenting muscles being activated on an exercising human body model to the exerciser allows the exerciser to exercise while paying attention to those muscles. Therefore, the exercise effect can be expected to be enhanced.

Figure 1:
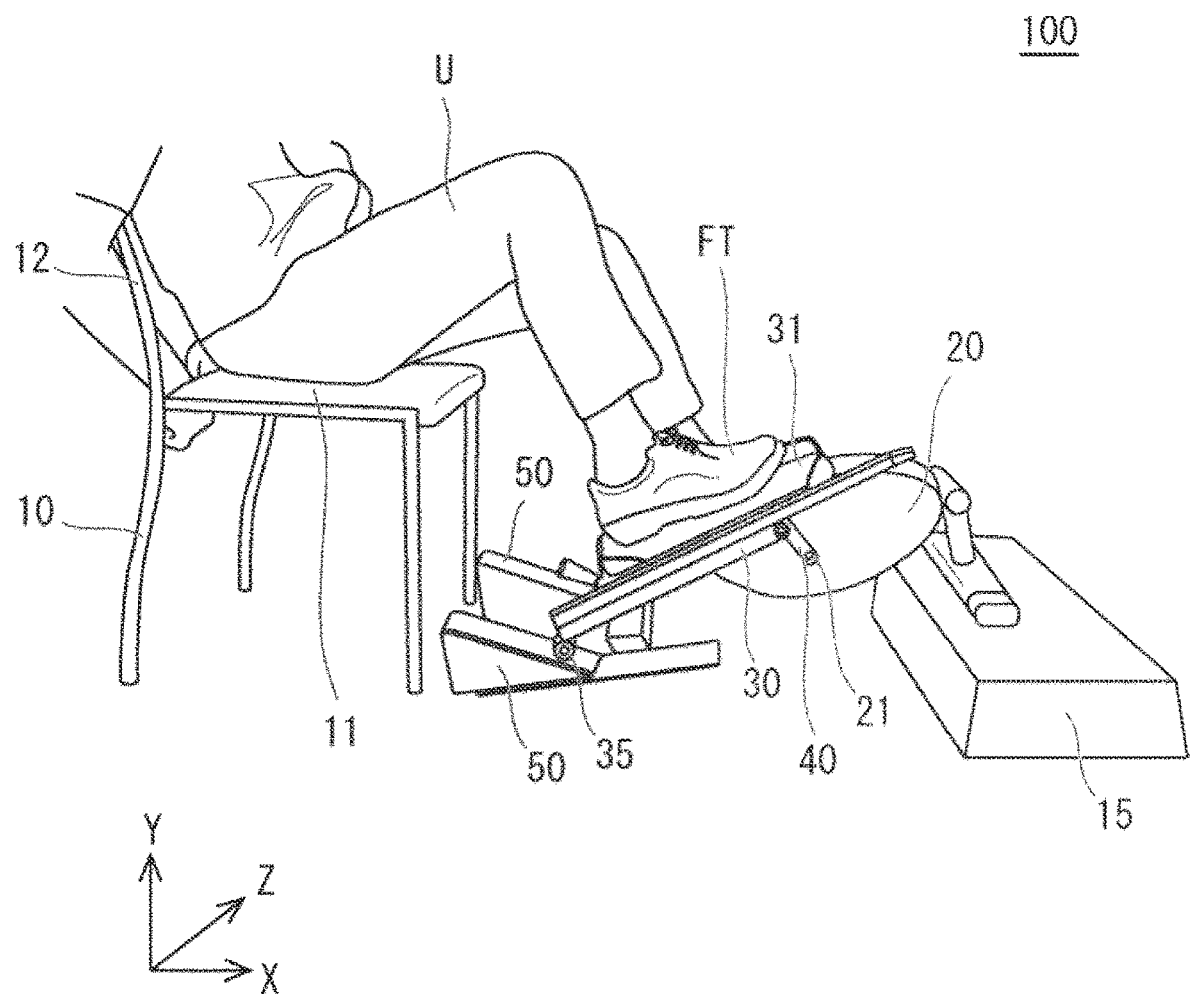
FIG. 1 is a side view of a pedal exercise device (first embodiment)
Figure 2:
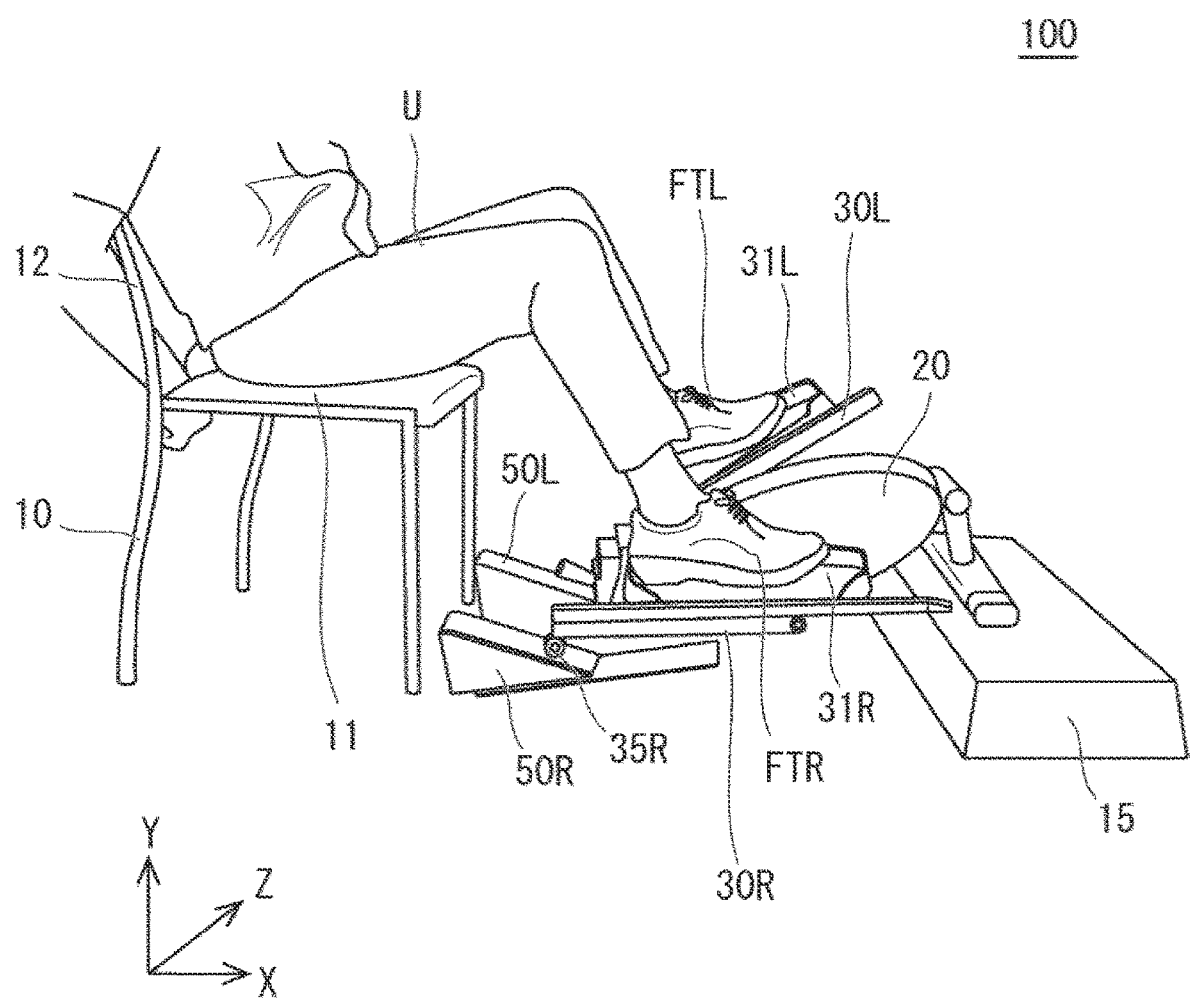
FIG. 2 is a side view of the pedal exercise device (first embodiment)

An exercise device 100 will be described with reference to FIGS. 1 and 2. FIGS. 1 and 2 show the exercise device 100 as viewed from the side. For the sake of clarity, the following description will be given using a three-dimensional XYZ Cartesian coordinate system. Specifically, the +X direction is an anterior (forward) direction, the –X direction is a posterior (backward) direction, the +Y direction is a superior (upward) direction, the –Y direction is an inferior (downward) direction, the +Z direction is a left direction, and the –Z direction is a right direction. The anteroposterior (front-back) direction, the lateral (left-right) direction, and the vertical (up-down) direction are the directions based on the normal direction of gaze of an exerciser U during exercise.

The exercise device 100 can adjust the range of motion of the ankle joint. In the following description, the rotational direction of the ankle joint about the Z axis is referred to as the "plantar/dorsal flexion direction," and the angle of this rotation is referred to as the "plantar/dorsal flexion angle." More specifically, the direction in which the toes of a foot FT are moved downward is referred to as the "plantarflexion direction," and the direction in which the toes of the foot FT are moved upward is referred to as the "dorsiflexion direction."

As shown in FIG. 1, the exercise device 100 includes a main body 20, a link 30, a crank (movable part) 40, and a tilted base 50. A chair 10 is placed behind the exercise device 100. The exerciser U performs a pedaling exercise while sitting on the chair 10. The exerciser U performs a pedaling exercise while being in a sitting position. The chair 10 therefore serves as a seating portion on which the exerciser U sits. The chair 10 may be integral with the exercise device 100, or may be a separate member from the exercise device 100. For example, the chair 10 may be a chair in a facility or home where the exerciser U is located. That is, the exerciser U or the assistant may place the chair 10 behind the exercise device 100.

The chair 10 includes a seat portion 11 that serves as a seating portion and a backrest portion 12. The backrest portion 12 supports the back of the exerciser U sitting on the seat portion 11. That is, the exerciser U can perform a pedaling exercise while leaning against the backrest portion 12. The chair 10 can be replaced or adjusted for the individual exerciser U. For example, an exerciser U who does heavier load training can use a chair 10 with no backrest portion 12. Alternatively, the backrest portion 12 may have a reclining mechanism. The angle of the backrest portion 12 may be adjusted by the reclining mechanism.

In the exercise device 100, components attached to the main body 20 are symmetrically. In FIG. 2, in order to distinguish between the right and left components, reference signs for the components on the right side of the main body 20 have the letter "R" at the end, and reference signs for the components on the left side of the main body 20 have the letter "L" at the end. For example, in FIG. 2, the left tilted base 50 is shown as a tilted base 50L, and the right tilted base 50 is shown as a tilted base 50R. Similarly, the left link 30 is shown as a link 30L, the left pedal 31 is shown as a pedal 31L, the right link 30 is shown as a link 30R, and the right pedal 31 is shown as a pedal 31R. Similarly, the left foot FT is shown as a left foot FTL, and the right foot FT is shown as a right foot FTR. In the following description, the letters "R" and "L" will be omitted when the right and left components are not distinguished from each other.

The main body 20 rotatably holds the crank 40. For example, the main body 20 is provided with a rotating shaft 21. The crank 40 is connected to the rotating shaft 21. The crank 40 extends in a direction perpendicular to the longitudinal direction of the rotating shaft 21. The crank 40 rotates about the rotating shaft 21. The main body 20 may have a load resistor that applies a load to the rotational motion of the crank 40. The main body 20 may have a gear etc. that can change the load.

The main body 20 is placed on an installation base 15. The installation base 15 is placed on the floor surface. For example, the front (anterior) part of the main body 20 is located on the installation base 15, and the back (posterior) part of the main body 20 is located on the floor surface. The installation angle of the main body 20 can be changed by changing the height, position, etc. of the installation base 15. For example, the main body 20 is placed horizontally by removing the installation base 15. The installation angle of the main body 20 is made steep by raising the installation base 15. The posture of the exerciser U during training is thus changed by changing the height of the installation base 15 or removing the installation base 15. The exerciser U's joint range of motion by training can thus be adjusted. With or without the installation base 15 is an example of exercise conditions of the exerciser U using the exercise device 100.

The distance between the main body 20 and the chair 10 in the anteroposterior direction may be changed according to the individual exerciser U. For example, the exerciser U can place the chair 10 near the main body 20. In this case, the exerciser U performs a pedaling exercise with his or her knee joints etc. relatively flexed. Alternatively, the exerciser U can place the chair 10 far from the main body 20. In this case, the exerciser U trains with his or her knee joints etc. relatively extended. The posture of the exerciser U during training is thus changed by changing the distance between the main body 20 and the chair 10 in the X direction. The exerciser U's joint range of motion by training can thus be adjusted. The distance between the main body 20 and the exercise device 100 in the anteroposterior direction is an example of the exercise conditions of the exerciser U using the exercise device 100.

The link 30 includes a pedal 31 and a sliding wheel 35. The crank 40 is connected to the front (anterior) end of the link 30, and the sliding wheel 35 is connected to the back (posterior) end of the link 30. The crank 40 and the link 30 are rotatably connected to each other. For example, the link 30 is attached to the crank 40 via a bearing etc. The pedal 31 is attached to an intermediate position on the link 30. The pedal 31 is a step (footrest) on which the exerciser U places his or her foot FT. The seated exerciser U places his or her foot FT on the pedal 31.

The sliding wheel 35 is attached to the link 30 via a rotating shaft (axle). That is, the link 30 rotatably holds the sliding wheel 35. The sliding wheel 35 is a sliding member that slides on a tilted surface of the tilted base 50.

The exerciser U performs a pedaling exercise with his or her foot FT on the pedal 31. That is, the exerciser U moves his or her knee joint, hip joint, and ankle joint so as to step on the pedal 31. As a result, the crank 40 rotates about the rotating shaft 21. The angle between the link 30 and the crank 40 changes according to the rotation of the crank 40. That is, the relative angle of the link 30 with respect to the crank 40 changes according to the rotation angle of the crank 40 (also referred to as the "crank angle"). The crank angle typically means the angle formed between a reference line extending forward (anteriorly) from the rotating shaft 21 and the crank 40. The sliding wheel 35 moves in the anteroposterior direction while in contact with the tilted surface. The crank 40 and the link 30 therefore rotate with the pedaling motion so that the pedal 31 follows an elliptical trajectory. That is, the exerciser U mainly applies a load to a plurality of muscles constituting the lower leg of the exerciser U by moving the foot FT placed on the pedal 31 along an elliptical trajectory defined by the exercise device 100.

The pedal 31, the sliding wheel 35, the link 30, the crank 40, and the tilted base 50 are provided for each of the right and left feet FT of the exerciser U. That is, the pedal 31, the sliding wheel 35, the link 30, the crank 40, and the tilted base 50 are provided on the right and left sides of the main body 20. The pedal 31R, the sliding wheel 35R, the link 30R, the tilted base 50R, etc. that are provided on the right side of the main body 20 are for the right foot FTR of the exerciser U. The pedal 31L, the link 30L, the tilted base 50L, etc. provided on the left side of the main body 20 are for the left foot FTL of the exerciser U.

The crank 40 is attached to the rotating shaft 21 of the main body 20 so as to be in antiphase between the right and left feet FT. That is, the rotation angle of the crank 40 for the left foot and the rotation angle of the crank 40 for the right foot are shifted by 180°. The exerciser U performs a pedaling exercise by alternately bending and extending his or her right and left legs.

The sliding wheel 35 is attached to the lower end of the link 30. The sliding wheel 35 has a wheel that slides on the tilted surface of the tilted base 50. The tilted base 50 has a tilted surface that is tilted upward toward the back (posterior). The sliding wheel 35 reciprocates in the X direction (anteroposterior direction) with the rotational motion of the link 30. As shown in FIG. 2, when the exerciser U is pedaling in such a direction that his or her right leg is extended and his or her left leg is bent, the right sliding wheel 35 moves forward (anteriorly) and the left sliding wheel 35 moves backward (posteriorly). As shown in FIG. 1, when the exerciser U is pedaling in such a direction that his or her left leg is extended and his or her right leg is bent, the left sliding wheel 35 moves forward (anteriorly) and the right sliding wheel 35 moves backward (posteriorly).

The height of the sliding wheel 35 changes along the tilted surface of the tilted base 50. The tilted surface of the tilted base 50 becomes higher toward the back (posterior). That is, the tilted base 50 is an uphill for the sliding wheel 35 moving backward (posteriorly). Therefore, the height of the sliding wheel 35 gradually increases as the sliding wheel 35 moves backward (posteriorly). The height of the sliding wheel 35 gradually decreases as the sliding wheel 35 moves forward (anteriorly). The angle of the link 30 is determined according to the height of the sliding wheel 35.

The angle of the pedal 31 located on the link 30 is limited according to the height of the sliding wheel 35. That is, the pedal 31 rotates in the plantarflexion direction as the height of the sliding wheel 35 increases. The pedal 31 rotates in the dorsiflexion direction as the height of the sliding wheel 35 decreases. Therefore, the range of motion for plantarflexion and dorsiflexion of the ankle joint can be adjusted according to the tilt angle of the tilted base 50. The range of motion for plantarflexion and dorsiflexion of the ankle joint can be adjusted according to the rotation angle of the crank 40. With or without the tilted base 50 and the tilt angle of the tilted base 50 are examples of the exercise conditions of the exerciser U using the exercise device 100.

The exerciser U performs a pedaling exercise with the exercise device 100 for training. That is, the pedaling exercise can place a load on the muscles of the lower limbs and trunk of the exerciser U. The muscles that can be built with the exercise device 100 include rectus abdominis, gluteus maximus, obturator externus, erector spinae, vastus *medialis*, vastus *intermedius*, rectus femoris, gastrocnemius, adductor *brevis*, biceps femoris, gluteus medius, plantaris, soleus, gluteus minimus, popliteus, tibialis anterior, iliacus, psoas major, and quadratus femoris. Of these muscle sites, gluteus medius, plantaris, soleus, gluteus minimus, popliteus, iliacus, psoas major, and quadratus femoris are deep muscles whose muscle activities cannot be measured with an electromyography sensor.

Exercise Conditions

The exercise conditions of the exerciser U using the exercise device 100 can be adjusted. That is, training can be effectively performed by adjusting various exercise conditions as appropriate. The muscle site that can be built by the pedaling exercise and the load amount to be placed on the muscle site can be adjusted by adjusting the various exercise conditions as appropriate. This allows effective training. The exercise conditions of the exerciser U using the exercise device 100 need not necessarily be set and changed by the exerciser U who trains, but may be set and changed by the assistant who assists the exerciser U in training. The assistant may be, for example, a physical therapist or an occupational therapist.

The exercise conditions of the exerciser U using the exercise device 100 can be divided into those related to the exercise device 100 and those related to the exerciser U.

The exercise conditions related to the exercise device 100 include, for example, the rotational speed of the crank 40, the load amount of the crank 40, and the rotational direction of the crank 40. For example, a heavy load can be placed on muscles by increasing the rotational speed of the crank 40 or increasing the load amount of the crank 40. The muscle site on which a load is placed can be changed by changing the rotational direction of the crank 40.

The exercise conditions related to the exercise device 100 include physical quantities that define the geometrical arrangement of the exercise device 100. Such exercise conditions include the distance between the chair 10 and the main body 20 in the anteroposterior direction, the installation angle (tilt angle) of the main body 20, the tilt angle of the pedal 31, the tilt angle of the tilted base 50, and the position of the tilted base 50 in the anteroposterior direction. The range of motion angle of the ankle joint can be changed according to the position of the tilted base 50 in the anteroposterior direction and the tilt angle of the tilted base 50. The range of motion angles of the knee joint and the hip joint are also changed by changing the distance between the main body 20 and the chair 10 in the anteroposterior direction, the tilt angle of the main body 20, etc. That is, the posture etc. during training can be changed by changing these exercise conditions. The muscle site to be built and the load amount to be placed on the muscle site can be adjusted by changing such exercise conditions.

The exercise conditions related to the exercise device 100 include with or without the backrest portion 12. For example, a chair 10 with a detachable backrest portion 12 is prepared, and the backrest portion 12 is removed when the exerciser U does heavy load training. Alternatively, a chair 10 with a backrest portion 12 and a chair 10 with no backrest portion 12 may be prepared, and the chair 10 may be replaced depending on the training.

The exercise conditions related to the exerciser U are typically conditions related to the postures and motions of the exerciser U. Specific examples of such exercise conditions include with or without crossed arms and with or without arm swinging motion. For example, the exerciser U can change the exercise conditions by selecting either with or without arm swinging motion while performing a pedaling exercise. Alternatively, the exerciser U can change the exercise conditions by selecting either with or without cross arms. The muscle site to be build can thus be changed according to the posture or motion of the exerciser U.

Figure 3:
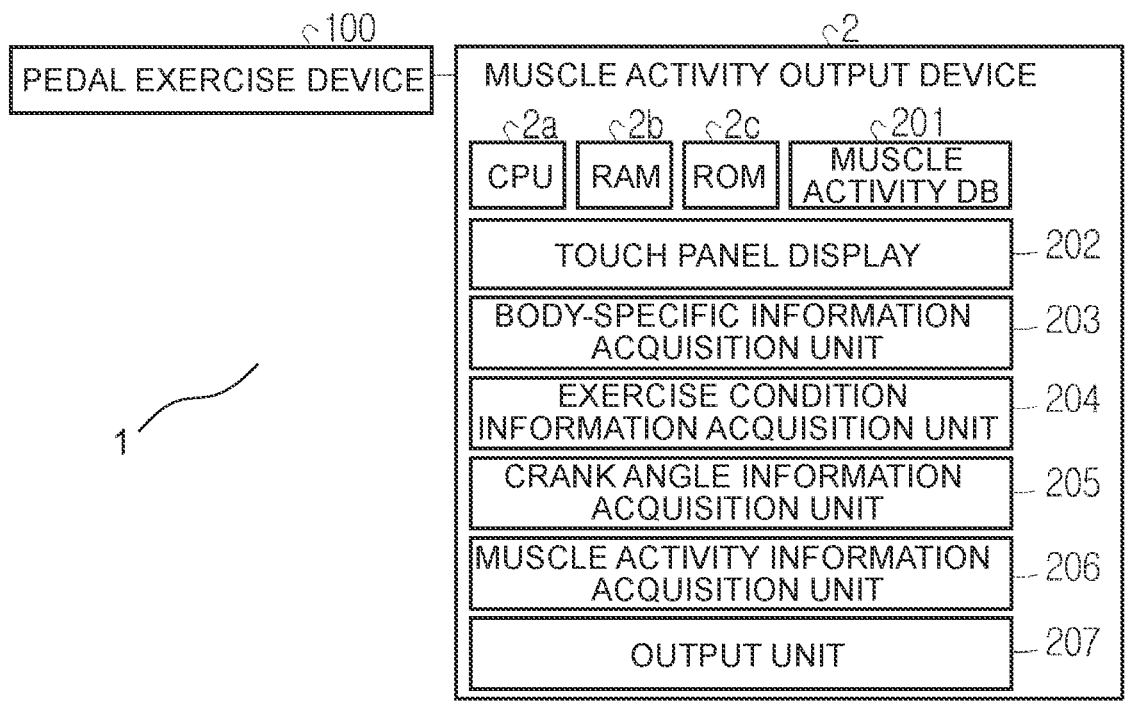
FIG. 3 is a functional block diagram of a muscle activity output system (first embodiment)

Next, a muscle activity output system 1 will be described with reference to FIG. 3. FIG. 3 is a functional block diagram of the muscle activity output system 1. As shown in FIG. 3, the muscle activity output system 1 includes a muscle activity output device 2 and the exercise device 100. The muscle activity output device 2 may be implemented by a single device, or may be implemented by distributed processing using a plurality of devices.

The muscle activity output device 2 includes a central processing unit (CPU) 2a as a central arithmetic processor (processor), a random access memory (RAM) 2b that is readable and writable, and a read-only memory (ROM) 2c that is only readable, a muscle activity database (DB) 201, and a touch panel display 202. The CPU 2a reads and executes a control program stored in the ROM 2c. The control program thus causes hardware such as the CPU to function as a plurality of functional units.

The functional units include a body-specific information acquisition unit 203, an exercise condition information acquisition unit 204, a crank angle information acquisition unit 205, a muscle activity information acquisition unit 206, and an output unit 207.

Figure 4:
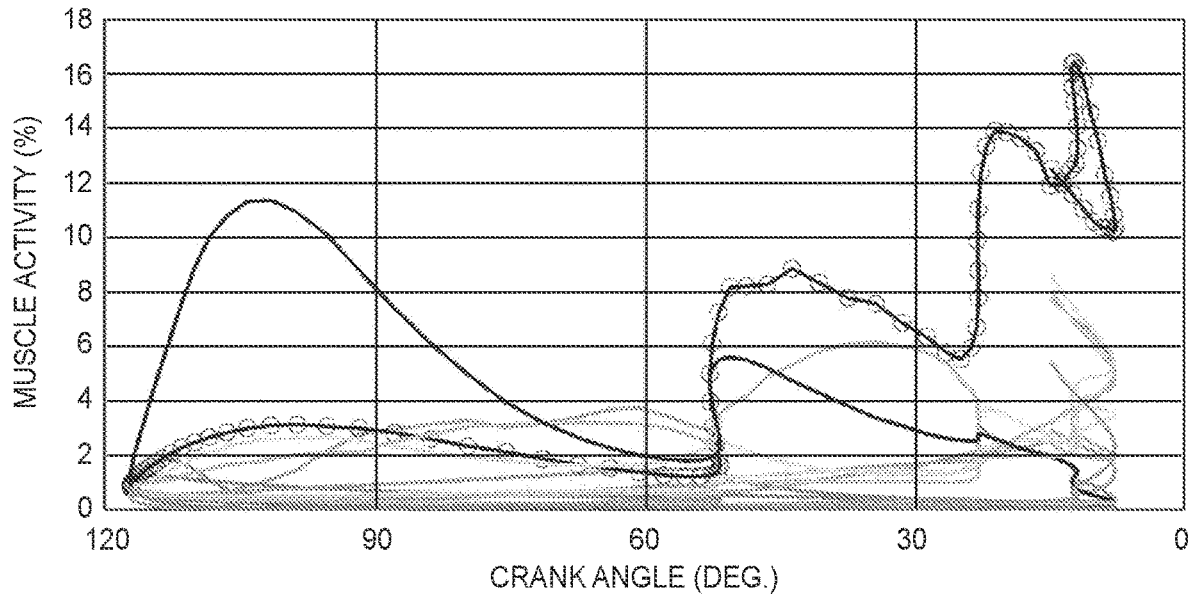
FIG. 4 illustrates the relationship between the crank angle and the muscle activity (first embodiment)

The muscle activity DB 201 is a database that holds crank angle information (movable part attitude information) and muscle activity information in such a manner that the crank angle information and the muscle activity information are linked to each other. The muscle activity information indicates the muscle activity of each muscle site of the exerciser U. Next, description will be given with reference to FIG. 4. FIG. 4 shows in a graph form the correspondence between the crank angle information and the muscle activity information when the height of the exerciser U is 175 cm, the rotational speed of the crank is 70 rpm, the load amount of the crank is 7 Nm, and the installation base 15 is not installed. The abscissa represents the crank angle, and the ordinate represents the muscle activity. As an example, the data on soleus is shown with markers (circles). As shown in FIG. 4, the muscle activity of each muscle site of the exerciser U changes with a change in crank angle. Specifically, the muscle activity DB 201 holds the muscle activity of each muscle site when the crank angle is 120 degrees, the muscle activity of each muscle site when the crank angle is 118 degrees, the muscle activity of each muscle site when the crank angle is 116 degrees, . . . , the muscle activity of each muscle site when the crank angle is 30 degrees, and the muscle activity of each muscle site when the crank angle is 10 degrees.

Next, description will be given with reference to FIG. 5. FIG. 5 shows in a graph form the correspondence between the crank angle information and the muscle activity information when the height of the exerciser U is 175 cm, the rotational speed of the crank is 90 rpm, the load amount of the crank is 3 Nm, and the installation base 15 is installed. The abscissa represents the crank angle, and the ordinate represents the muscle activity of each muscle site of the exerciser U. As an example, the data on soleus is shown with markers (circles). As shown in FIGS. 4 and 5, when the exercise conditions of the exerciser U using the exercise device 100 change, the correspondence between the crank angle information and the muscle activity information indicating the muscle activity of each muscle site of the exerciser U also changes significantly. Similarly, when the height of the exerciser U changes, the correspondence between the crank angle information and the muscle activity information indicating the muscle activity of each muscle site of the exerciser U also changes significantly.

In the muscle activity DB 201, the correspondence between the crank angle information and the muscle activity information indicating the muscle activity of each muscle site of the exerciser U is therefore held for each exerciser U's height and each set of exercise conditions of the exerciser U using the exercise device 100.

FIG. 6 illustrates the structure of the muscle activity DB 201. In FIG. 6, the height means the height of the exerciser U. The crank rotational speed, the crank load amount, the crank rotational direction, and exercise conditions 4 to 16 mean the exercise conditions of the exerciser U using the exercise device 100. Correspondence information is information indicating such correspondence between the crank angle information and the muscle activity information indicating the muscle activity of each muscle site of the exerciser U that can be represented in a graph form as in FIGS. 4 and 5. In the example of FIG. 6, the muscle activity DB 201 includes data for the height of 145 cm, 150 cm, 155 cm, 160 cm, and 165 cm. However, the muscle activity DB 201 may actually include data for the height of 170 cm, 175 cm, 180 cm, and 185 cm. The muscle activity DB 201 includes data for the crank rotational speed of 30 rpm, 40 rpm, 50 rpm, and 60 rpm. However, the muscle activity DB 201 may actually include data for the crank rotational speed of 70 rpm, 80 rpm, 90 rpm, and 100 rpm. The muscle activity DB 201 includes data for the crank load amount of 0.1 Nm, 0.3 Nm, 0.5 Nm, 0.8 Nm, 1.0 Nm, 1.3 Nm, and 1.5 Nm.

However, the muscle activity DB 201 may actually include data for the crank load amount of 3 Nm, 5 Nm, 7 Nm, 9 Nm, 11 Nm and 13 Nm. The muscle activity DB 201 includes data for forward rotation and reverse rotation as the crank rotational direction. The muscle activity DB 201 holds a huge amount of correspondence information for various combinations of height, crank rotational speed, crank load amount, crank rotational direction, and other exercise conditions. In the example of FIG. 6, the muscle activity DB 201 holds the correspondence information for two million combinations.

The correspondence information for the two million combinations held in the muscle activity DB 201 can be generated by, for example, a simulator using a human body computer model (e.g., a human body model such as a human body finite element model). That is, the simulator generates a human body model and an exercise device model based on body-specific information and exercise condition information, and calculates a change in muscle activity of each muscle site that occurs with a change in crank angle.

The touch panel display 202 is an integrated unit composed of a touch panel and a display. The exerciser U or the assistant can enter the height of the exerciser U and the exercise conditions of the exerciser U using the exercise device 100 to the muscle activity output device 2 via the touch panel display 202. FIG. 7 shows a display example of the touch panel display 202.

The body-specific information acquisition unit 203 acquires body-specific information of the exerciser U. In the present embodiment, the body-specific information acquisition unit 203 outputs to the touch panel display 202, a message 202*a* prompting to enter the height of the exerciser U. The exerciser U or the assistant enters the height of the exerciser U to the muscle activity output device 2 via the touch panel display 202. The body-specific information acquisition unit 203 thus acquires the body-specific information indicating the height of the exerciser U. The height of the exerciser U is a specific example of the body-specific information of the exerciser U. The body-specific information of the exerciser U may be the inseam of the exerciser U instead of the height of the exerciser U.

The muscle activity output device 2 may include a database that holds the correspondence between the identification (ID) of the exerciser U and the body-specific information of the exerciser U. In this case, the body-specific information acquisition unit 203 may output to the touch panel display 202, a message prompting to enter the identification (ID) of the exerciser U, acquire the identification (ID) of the exerciser U entered via the touch panel display 202 by the exerciser U or the assistant, and search the database for the acquired identification (ID) to acquire the body-specific information of the exerciser U.

The exercise condition information acquisition unit 204 acquires exercise condition information indicating the exercise conditions of the exerciser U using the exercise device 100. In the present embodiment, the exercise condition information acquisition unit 204 outputs to the touch panel display 202, a message 202*b* prompting to enter the exercise conditions for the exercise device 100. The exerciser U or the assistant enters the exercise conditions of the exerciser U using the exercise device 100 to the muscle activity output device 2 via the touch panel display 202. The exercise condition information acquisition unit 204 thus acquires the exercise condition information.

Returning back to FIG. 3, the crank angle information acquisition unit 205 acquires the crank angle information in real time by receiving the crank angle information from the exercise device 100 connected to the muscle activity output device 2.

The muscle activity information acquisition unit 206 acquires the current muscle activity information for each muscle site based on the current crank angle information of the exercise device 100 and the muscle activity DB 201. Specifically, the muscle activity information acquisition unit 206 identifies the correspondence information to be referred to in the muscle activity DB 201 based on the body-specific information and the exercise condition information, and refers to the identified correspondence information. The muscle activity information acquisition unit 206 thus acquires the current muscle activity information for each muscle site corresponding to the current crank angle of the exercise device 100. A part of the body-specific information and exercise condition information is discrete. Therefore, when identifying the correspondence information to be referred to in the muscle activity DB 201 based on the body-specific information acquired by the body-specific information acquisition unit 203 and the exercise condition information acquired by the exercise condition information acquisition unit 204, the muscle activity information acquisition unit 206 can search the muscle activity DB 201 for body-specific information closest to the body-specific information acquired by the body-specific information acquisition unit 203, and search the muscle activity DB 201 for exercise condition information closest to the exercise condition information acquired by the exercise condition information acquisition unit 204.

The output unit 207 outputs the current muscle activity information of each muscle site to the touch panel display 202. In the present embodiment, as shown in FIG. 7, the output unit 207 displays a human body muscle anatomy model 202*c* on the touch panel display 202, and colors each muscle site differently according to its muscle activity. For example, a muscle site whose muscle activity is 100% is colored in red, a muscle site whose muscle activity is 50% is colored in green, and a muscle site whose muscle activity is 0% is colored in blue. By checking the color of each muscle site of the human body muscle anatomy model 202*c*, the exerciser U or the assistant can be aware of the current muscle activity of each muscle site. That is, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

Figure 8:
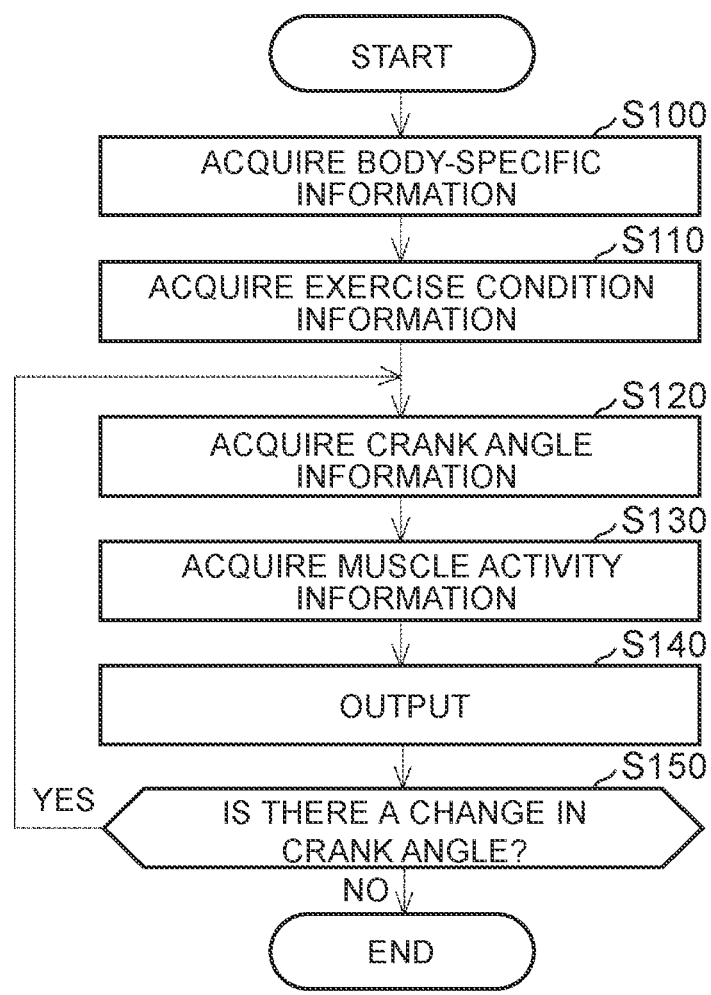
FIG. 8 is a flowchart of the operation of the muscle activity output system (first embodiment)

Next, the operation of the muscle activity output system 1 will be described with reference to FIG. 8. FIG. 8 is a flowchart of the operation of the muscle activity output system 1.

Step S100

First, the body-specific information acquisition unit 203 acquires body-specific information indicating the height of the exerciser U.

Step S110

Next, the exercise condition information acquisition unit 204 acquires exercise condition information indicating the exercise conditions of the exerciser U using the exercise device 100.

Step S120

The crank angle information acquisition unit 205 then acquires crank angle information indicating the crank angle of the crank 40 of the exercise device 100.

Step S130

Thereafter, the muscle activity information acquisition unit 206 refers to the muscle activity DB 201 and acquires current muscle activity information for each muscle site based on the body-specific information, the exercise condition information, and the crank angle information.

Step S140

Subsequently, the output unit 207 outputs the current muscle activity information of each muscle site to the touch panel display 202.

Step S150

The muscle activity output device 2 then determines whether there is a change in crank angle. When there is no change in crank angle (step S150: NO), the muscle activity output device 2 ends the process. On the other hand, when there is a change in crank angle (step S150: YES), the routine returns to step S120. The muscle activity output device 2 performs the series of steps from step S120 to step S150, for example, once per second.

The first embodiment is described above, and the first embodiment has the following features.

The muscle activity output system 1 includes the muscle activity DB 201 (muscle activity database). The muscle activity DB 201 holds the crank angle information (movable part attitude information) and the muscle activity information in such a manner that the crank angle information and the muscle activity information are linked to each other. The crank angle information indicates the crank angle (attitude) of the crank 40 (movable part) of the exercise device 100 (training equipment) when the exerciser U moves his or her body along a trajectory defined by the exercise device 100 that is a device that applies a load to muscles of the exerciser U. The muscle activity information indicates the muscle activity of each muscle site of the exerciser U. The muscle activity output system 1 includes the crank angle information acquisition unit 205 (movable part attitude information acquisition unit) that acquires the crank angle information in real time while the exerciser U is moving his or her body along the trajectory. The muscle activity output system 1 includes the muscle activity information acquisition unit 206 that acquires the current muscle activity information for each muscle site based on the current crank angle information of the exercise device 100 and the muscle activity DB 201. The muscle activity output system 1 includes the output unit 207 that outputs the current muscle activity information of each muscle site. According to the above configuration, the exerciser U or the assistant can be aware of the current muscle activity of each muscle site including deep muscles. The exerciser U or the assistant can therefore check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved. Moreover, presenting muscles being activated on an exercising human body model to the exerciser U allows the exerciser U to exercise while paying attention to those muscles. Therefore, the exercise effect can be expected to be enhanced.

That is, since the exerciser U exercises while paying attention to the muscles to be moved, the muscle contraction time increases. This is known to enhance the effect of strength training. Presenting the muscles to be moved to the exerciser U allows the exerciser U to exercise while paying attention to those muscles. Therefore, the exercise effect can be expected to be enhanced. It is also possible to present stresses applied between joints and stresses applied to bones during exercise. The database holds information on loads placed on joints and bones during exercise. Therefore, by presenting the levels of stress applied to bones and joints in addition to muscle activities, a person who is at a high risk of injury when loads are applied to bones and joints during exercise can be careful not to do an exercise too hard for him or her.

As an example, the training equipment is the pedal exercise device 100 with which the exerciser U performs a pedaling exercise while being in a sitting position. The movable part attitude information of the training equipment is the crank angle information indicating the crank angle of the pedal exercise device 100.

The muscle activity DB 201 holds the crank angle information and the muscle activity information in such a manner that the crank angle information and the muscle activity information are linked to the exercise condition information indicating the exercise conditions of the exerciser U. The muscle activity output system 1 further includes the exercise condition information acquisition unit 204 that acquires the exercise condition information. The muscle activity information acquisition unit 206 acquires the current muscle activity information for each muscle site based on the current crank angle information of the exercise device 100, the exercise condition information, and the muscle activity DB 201. With the above configuration, the exerciser U or the assistant can be accurately aware of the current muscle activity of each muscle site including deep muscles.

The muscle activity DB 201 holds the crank angle information and the muscle activity information in such a manner that the crank angle information and the muscle activity information are linked to the body-specific information of the exerciser U. The muscle activity output system 1 further includes the body-specific information acquisition unit 203 that acquires the body-specific information. The muscle activity information acquisition unit 206 acquires the current muscle activity information for each muscle site based on the current crank angle information of the exercise device 100, the body-specific information, and the muscle activity DB 201. With the above configuration, the exerciser U or the assistant can be accurately aware of the current muscle activity of each muscle site including deep muscles.

The muscle activity DB 201 holds at least the crank angle information and the muscle activity information indicating the muscle activities of deep muscles of the exerciser U in such a manner that the crank angle information and the muscle activity information are linked to each other. With the above configuration, since the exerciser U or the assistant can be aware of the current muscle activities of deep muscles, the exerciser U or the assistant can check whether deep muscles to be activated have been activated and deep muscles not to be activated have not been activated. Accordingly, the exerciser U or the assistant can check whether the exercise the exerciser U is performing is an exercise that suits the exerciser U's purpose. As a result, an effective exercise is achieved.

The muscle activity output method uses the muscle activity DB 201 (muscle activity database) that holds the crank angle information (movable part attitude information) and the muscle activity information in such a manner that the crank angle information and the muscle activity information are linked to each other. The crank angle information indicates the crank angle (attitude) of the crank 40 (movable part) of the exercise device 100 (training equipment) when the exerciser U moves his or her body along a trajectory defined by the exercise device 100 that is a device that applies a load to muscles of the exerciser U. The muscle activity information indicates the muscle activity of each muscle site of the exerciser U. The muscle activity output method includes the movable part attitude information acquisition step (step S120) of acquiring the crank angle information in real time while the exerciser U is moving his or her body. The muscle activity output method includes the muscle activity information acquisition step (step S130) of acquiring the current muscle activity information for each muscle site based on the current crank angle information of the exercise device 100 and the muscle activity DB 201. The muscle activity output method includes the output step (step S140) of outputting the current muscle activity information for each muscle site. With the above method, since the exerciser U or the assistant can be aware of the current muscle activity of each muscle site including deep muscles, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

In the present embodiment, the output unit 207 outputs the current muscle activity information of each muscle site to the touch panel display 202. However, the output unit 207 may alternatively output the current muscle activity information for each muscle site by voice via a speaker, not shown. The output unit 207 may output the current muscle activity information for each muscle site via a vibration motor, not shown, attached to the body of the exerciser U. In this case, whether the muscle site is a superficial muscle or a deep muscle and the muscle activity of the muscle site may be represented by changing the frequency, attitude, or duty cycle of the vibration motor.

Second Embodiment

Next, a second embodiment of the present disclosure will be described with reference to FIGS. 9 and 10. The differences of the present embodiment from the first embodiment will be mainly described, and duplicated description will be omitted.

In the first embodiment, the muscle activity output device 2 receives crank angle information from the exercise device 100 and refers to the muscle activity DB 201 to acquire muscle activity information corresponding to the received crank angle information.

On the other hand, the muscle activity output device 2 of the present embodiment receives body posture information from a sensor attached to the exerciser U. The muscle activity output device 2 converts the received body posture information to crank angle information and refers to the muscle activity DB 201 to acquire muscle activity information corresponding to the obtained crank angle information.

Figure 9:
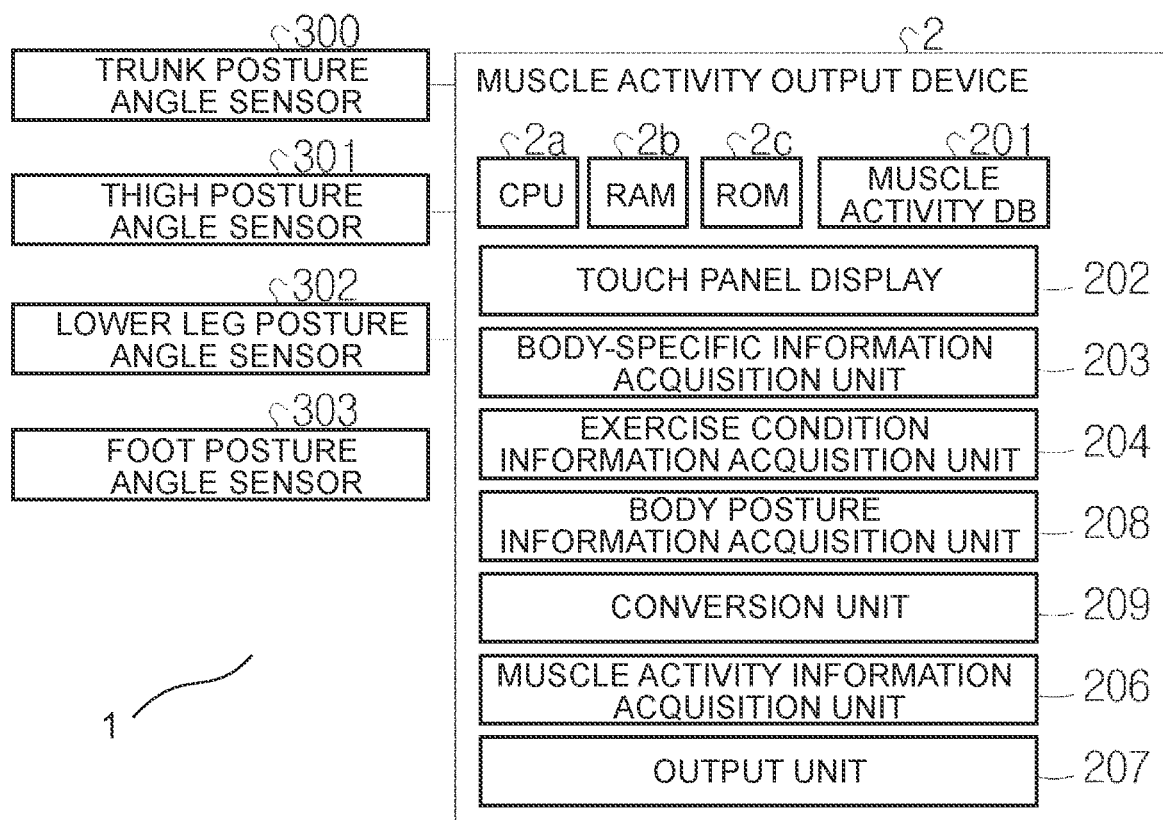
FIG. 9 is a functional block diagram of a muscle activity output system (second embodiment)

FIG. 9 shows the muscle activity output system 1 of the present embodiment. The muscle activity output device 2 includes a body posture information acquisition unit 208 and a conversion unit 209, instead of the crank angle information acquisition unit 205.

A trunk posture angle sensor 300, a thigh posture angle sensor 301, a lower leg posture angle sensor 302, and a foot posture angle sensor 303 are attached to the exerciser U.

Specifically, the trunk posture angle sensor 300 is attached to the trunk of the exerciser U. The trunk posture angle sensor 300 outputs trunk posture information indicating the posture of the trunk of the exerciser U to the muscle activity output device 2.

The thigh posture angle sensor 301 is attached to a thigh of the exerciser U. The thigh posture angle sensor 301 outputs thigh posture information indicating the posture of the thigh of the exerciser U to the muscle activity output device 2.

The lower leg posture angle sensor 302 is attached to a lower leg of the exerciser U. The lower leg posture angle sensor 302 outputs lower leg posture information indicating the posture of the lower leg of the exerciser U to the muscle activity output device 2.

The foot posture angle sensor 303 is attached to a foot of the exerciser U. The foot posture angle sensor 303 outputs foot posture information indicating the posture of the foot of the exerciser U to the muscle activity output device 2.

Each of the trunk posture angle sensor 300, the thigh posture angle sensor 301, the lower leg posture angle sensor 302, and the foot posture angle sensor 303 is typically a posture sensor composed of a gyroscope and a three-axis acceleration sensor.

The body posture information acquisition unit 208 receives and acquires the trunk posture information, the thigh posture information, the lower leg posture information, and the foot posture information from the trunk posture angle sensor 300, the thigh posture angle sensor 301, the lower leg posture angle sensor 302, and the foot posture angle sensor 303, respectively. The body posture information acquisition unit 208 calculates hip joint angle information indicating the pitch angle of the hip joint from the trunk posture information and the thigh posture information. The body posture information acquisition unit 208 calculates knee joint angle information indicating the pitch angle of a knee joint from the thigh posture information and the lower leg posture information. The body posture information acquisition unit 208 calculates ankle joint angle information indicating the pitch angle of an ankle joint from the lower leg posture information and the foot posture information.

The trunk posture information, the hip joint angle information, the knee joint angle information, and the ankle joint angle information constitute body posture information. The body posture information includes at least one of the following pieces of information: the trunk posture information, the hip joint angle information, the knee joint angle information, and the ankle joint angle information. The body posture information preferably includes at least the hip joint angle information and the knee joint angle information. This is because the crank angle is roughly obtained from the hip joint angle information and the knee joint angle information.

The method for the body posture information acquisition unit 208 to acquire the body posture information is not limited to the above method. For example, the trunk posture information, the thigh posture information, the lower leg posture information, and the foot posture information can be obtained by placing motion capture markers on the trunk, thigh, lower leg, and foot of the exerciser U and identifying the positions of the markers with a three-dimensional measurement camera.

The conversion unit 209 converts the body posture information to crank angle information. Specifically, the conversion unit 209 geometrically calculates a current crank angle based on the current trunk posture information, hip joint angle information, knee joint angle information, and ankle joint angle information. The conversion unit 209 may calculate a current crank angle based on the current trunk posture information, hip joint angle information, knee joint angle information, and ankle joint angle information by considering the body-specific information indicating the height of the exerciser U and the exercise conditions of the exerciser U using the exercise device 100.

Next, the operation of the muscle activity output system 1 will be described with reference to FIG. 10. FIG. 10 is a flowchart of the operation of the muscle activity output system 1.

Figure 10:
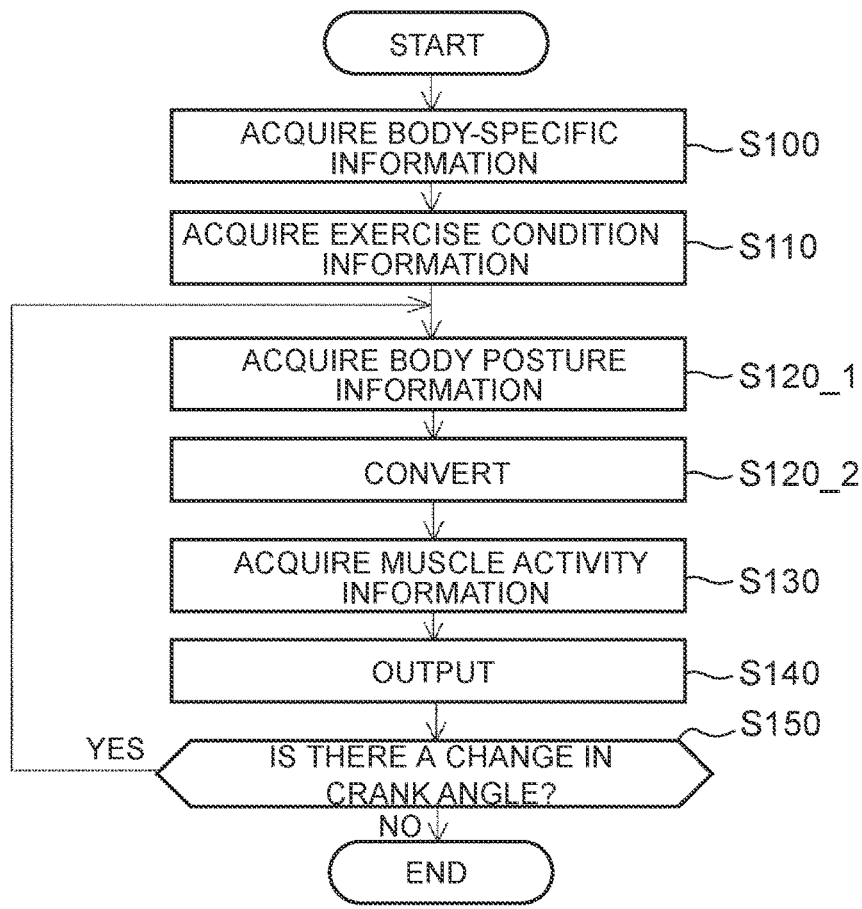
FIG. 10 is a flowchart of the operation of the muscle activity output system (second embodiment)

In the control flow of the muscle activity output device 2 of the present embodiment shown in FIG. 10, step S120 of the first embodiment shown in FIG. 8 is replaced with step S120_1 and step S120_2.

Step S120_1

After step S110 is completed, the body posture information acquisition unit 208 acquires body posture information.

Step S120_2

The conversion unit 209 then converts the body posture information to crank angle information.

The second embodiment is described above, and the second embodiment has the following features.

The muscle activity output system 1 includes the muscle activity DB 201 (muscle activity database) that holds the crank angle information (movable part attitude information) and the muscle activity information in such a manner that the crank angle information and the muscle activity information are linked to each other. The crank angle information indicates the crank angle (attitude) of the crank 40 (movable part) of the exercise device 100 (training equipment) when the exerciser U moves his or her body along a trajectory defined by the exercise device 100 that is a device that applies a load to muscles of the exerciser U. The muscle activity information indicates the muscle activity of each muscle site of the exerciser U. The muscle activity output system 1 includes the body posture information acquisition unit 208 that acquires the body posture information of the exerciser U in real time while the exerciser U is moving his or her body along the trajectory. The muscle activity output system 1 includes the conversion unit 209 that converts the body posture information to crank angle information. The muscle activity output system 1 includes the muscle activity information acquisition unit 206 that acquires the current muscle activity information for each muscle site based on the current crank angle information of the exercise device 100 and the muscle activity DB 201. The muscle activity output system 1 includes the output unit 207 that outputs the current muscle activity information of each muscle site. With the above configuration, since the exerciser U or the assistant can be aware of the current muscle activity of each muscle site including deep muscles, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

The muscle activity output method uses the muscle activity DB 201 (muscle activity database) that holds the crank angle information (movable part attitude information) and the muscle activity information in such a manner that the crank angle information and the muscle activity information are linked to each other. The crank angle information indicates the crank angle (attitude) of the crank 40 (movable part) of the exercise device 100 (training equipment) when the exerciser U moves his or her body along a trajectory defined by the exercise device 100 that is a device that applies a load to muscles of the exerciser U. The muscle activity information indicates the muscle activity of each muscle site of the exerciser U. The muscle activity output method includes the body posture information acquisition step (step S120_1) of acquiring the body posture information of the exerciser U in real time while the exerciser U is moving his or her body. The muscle activity output method includes the conversion step (step S120_2) of converting the body posture information to crank angle information. The muscle activity output method includes the muscle activity information acquisition step (step S130) of acquiring the current muscle activity information for each muscle site based on the current crank angle information of the exercise device 100 and the muscle activity DB 201. The muscle activity output method includes the output step (step S140) of outputting the current muscle activity information for each muscle site. With the above method, since the exerciser U or the assistant can be aware of the current muscle activity of each muscle site including deep muscles, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

Third Embodiment

Next, a third embodiment will be described with reference to FIGS. 11 and 12. The differences of the present embodiment from the first embodiment will be mainly described, and duplicated description will be omitted.

In the first embodiment, it is assumed that the exerciser U exercises using the exercise device 100 as training equipment. On the other hand, in the present embodiment, it is assumed that the exerciser U does not exercise using training equipment but exercises by moving his or her body along a predetermined trajectory.

The predetermined trajectory is typically a trajectory determined for each bodyweight training. Examples of the bodyweight training include front bridge, plank leg raise, normal push-up, crunch, bicycle crunch, narrow push-up, reverse push-up, squat, pull-up, back extension, high reverse plank, and standing calf raise. Each bodyweight training defines which part of the body is moved back and forth along what trajectory. The predetermined trajectory may be a trajectory specified by an instructor in real time with his or her movement.

Figure 11:
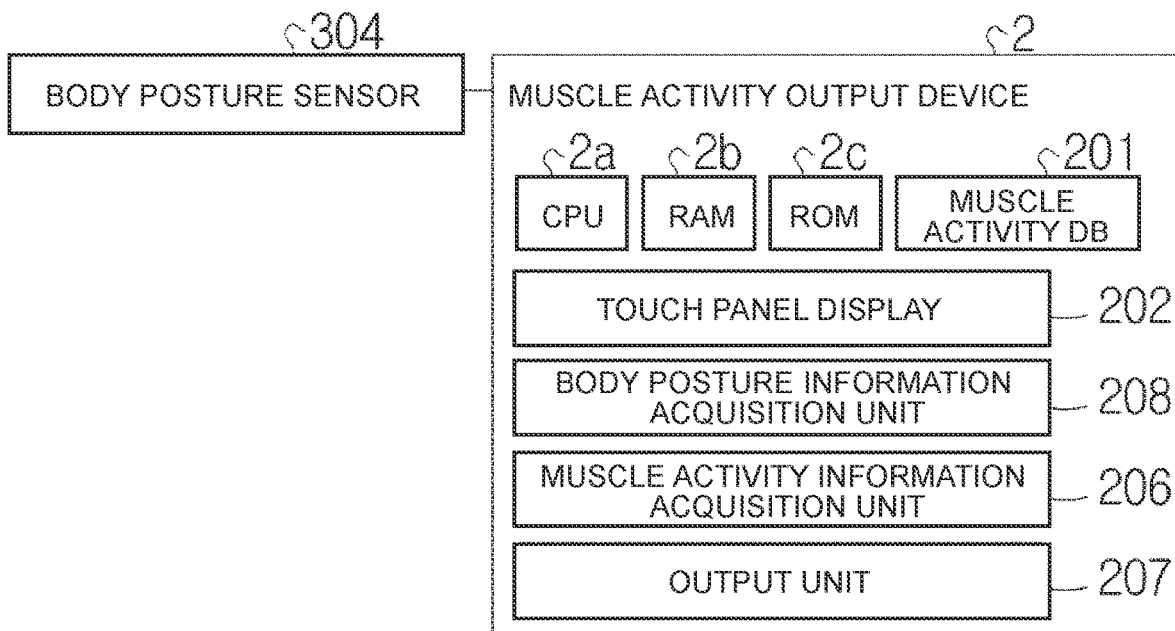
FIG. 11 is a functional block diagram of a muscle activity output system (third embodiment)
Figure 12:
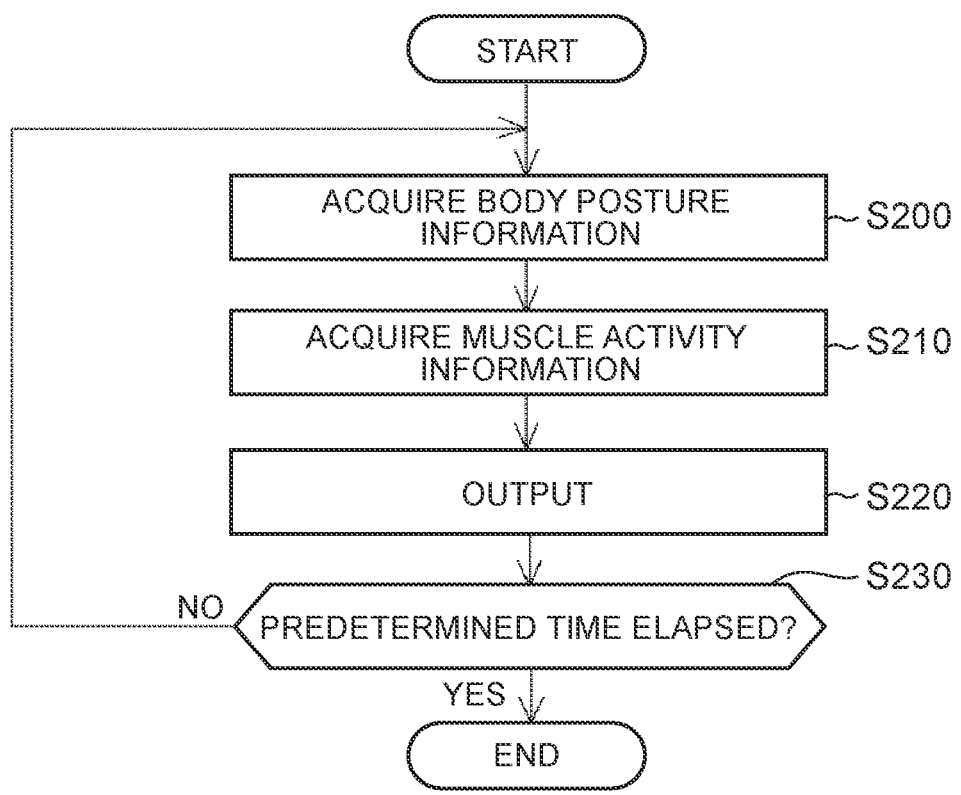
FIG. 12 is a flowchart of the operation of the muscle activity output system (third embodiment).

FIG. 11 shows a functional block diagram of the muscle activity output system 1 of the present embodiment. As shown in FIG. 11, the muscle activity output device 2 of the present embodiment includes the muscle activity DB 201, the touch panel display 202, the body posture information acquisition unit 208, the muscle activity information acquisition unit 206, and the output unit 207.

In the first embodiment, the muscle activity DB 201 is a database that holds the crank angle information and the muscle activity information indicating the muscle activity of each muscle site of the exerciser U in such a manner that the crank angle information and the muscle activity information are linked to each other. On the other hand, the muscle activity DB 201 of the present embodiment is a database that holds the body posture information and the muscle activity information indicating the muscle activity of each muscle site of the exerciser U in such a manner that the body posture information and the muscle activity information are linked to each other. The body posture is, for example, the joint angle of a joint of the body of the exerciser U. In the present embodiment, examples of the body posture includes a neck joint angle, a shoulder joint angle, an elbow joint angle, trunk posture information, a hip joint angle, a knee joint angle, and an ankle joint angle. As an example, the muscle activity DB 201 holds the body posture information indicating the elbow joint angle and the muscle activity information indicating the muscle activity of each muscle site of the exerciser U in such a manner that the body posture information and the muscle activity information are linked to each other. The muscle activity DB 201 can be generated by a simulator using a human body computer model as in the above embodiment.

The body posture information acquisition unit 208 receives and acquires body posture information from a body posture sensor 304. The body posture sensor 304 may be a sensor that measures in a contactless manner the positions of markers attached to various body parts of the exerciser U. Alternatively, posture sensors may be placed on various body parts of the exerciser U, and the body posture sensor 304 may receive and acquire body posture information from the posture sensors.

The muscle activity information acquisition unit 206 refers to the muscle activity DB 201 and acquires current muscle activity information for each muscle site based on the body posture information.

The output unit 207 outputs the current muscle activity information of each muscle site to the touch panel display 202.

Next, the operation of the muscle activity output system 1 will be described with reference to FIG. 12. FIG. 12 is a flowchart of the operation of the muscle activity output system 1.

Step S200

First, the body posture information acquisition unit 208 acquires the body posture information.

Step S210

Next, the muscle activity information acquisition unit 206 refers to the muscle activity DB 201 and acquires current muscle activity information for each muscle site based on the body posture information.

Step S220

The output unit 207 then outputs the current muscle activity information of each muscle site to the touch panel display 202.

Step S230

Subsequently, the muscle activity output device 2 determines whether a predetermined time has elapsed. When the predetermined time has elapsed (step S230: YES), the muscle activity output device 2 ends the process. On the other hand, when the predetermined time has not elapsed (step S230: NO), the routine returns to step S200.

The third embodiment is described above, and the third embodiment has the following features.

The muscle activity output system 1 includes the muscle activity DB 201 (muscle activity database) that holds the body posture information and the muscle activity information in such a manner that the body posture information and the muscle activity information are linked to each other, the body posture information indicating the body posture of the exerciser U when the exerciser U moves his or her body along a predetermined trajectory, and the muscle activity information indicating the muscle activity of each muscle site of the exerciser U. The muscle activity output system 1 includes the body posture information acquisition unit 208 that acquires the body posture information in real time while the exerciser U is moving his or her body along the trajectory. The muscle activity output system 1 includes the muscle activity information acquisition unit 206 that acquires the current muscle activity information for each muscle site based on the current body posture information of the exerciser U and the muscle activity DB 201. The muscle activity output system 1 includes the output unit 207 that outputs the current muscle activity information of each muscle site. With the above configuration, since the exerciser U or the assistant can be aware of the current muscle activity of each muscle site including deep muscles, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

The body posture of the exerciser U includes the joint angle of a joint of the body of the exerciser U.

The muscle activity DB 201 holds at least the body posture information and the muscle activity information indicating the muscle activities of deep muscles of the exerciser U in such a manner that the body posture information and the muscle activity information are linked to each other. With the above configuration, since the exerciser U or the assistant can be aware of the current muscle activities of deep muscles, the exerciser U or the assistant can check whether deep muscles to be activated have been activated and deep muscles not to be activated have not been activated. Accordingly, the exerciser U or the assistant can check whether the exercise the exerciser U is performing is an exercise that suits the exerciser U's purpose. As a result, an effective exercise is achieved.

The muscle activity output method uses the muscle activity DB 201 (muscle activity database) that holds the body posture information and the muscle activity information in such a manner that the body posture information and the muscle activity information are linked to each other, the body posture information indicating the body posture of the exerciser U when the exerciser U moves his or her body along a predetermined trajectory, and the muscle activity information indicating the muscle activity of each muscle site of the exerciser U. The muscle activity output method includes the body posture information acquisition step (step S200) of acquiring the body posture information in real time while the exerciser U is moving his or her body along the trajectory. The muscle activity output method includes the muscle activity information acquisition step (step S210) of acquiring the current muscle activity information for each muscle site based on the current body posture information of the exerciser U and the muscle activity DB 201. The muscle activity output method includes the output step (step S220) of outputting the current muscle activity information of each muscle site. With the above method, since the exerciser U or the assistant can be aware of the current muscle activity of each muscle site including deep muscles, the exerciser U or the assistant can check whether muscle sites to be activated have been activated and muscle sites not to be activated have not been activated. Accordingly, the exerciser U or the assistant can check whether the exercise the exerciser U is performing is an exercise that suits the exerciser U's purpose. As a result, an effective exercise is achieved.

In the examples described above, the program can be stored using various types of non-transitory computer-readable media (non-transitory storage media) and supplied to a computer. The non-transitory computer-readable media include various types of tangible storage media. Examples of the non-transitory computer-readable media include magnetic recording media (e.g., flexible disks, magnetic tapes, and hard disk drives), and magneto-optical recording media (e.g., magneto-optical disks). Other examples of the non-transitory computer-readable media include compact disc read-only memories (CD-ROMs), compact disc-recordable discs (CD-Rs), compact disc-rewritable discs (CD-R/Ws), and semiconductor memories (e.g., mask ROMs). Other examples of the non-transitory computer-readable media include programmable ROMs (PROMs), erasable PROMs (EPROMs), flash ROMs, and random access memories (RAMs). The program may be supplied to the computer by various types of transitory computer-readable media. Examples of the transitory computer-readable media include electrical signals, optical signals, and electromagnetic waves. The transitory computer-readable media can supply the program to the computer via a wired communication path such as an electric wire and an optical fiber, or a wireless communication path.

The present disclosure is not limited to the above embodiments, and can be modified as appropriate without departing from the spirit and scope of the present disclosure.

What is claimed is:

1. A muscle activity output system, comprising:
a memory storing a muscle activity database that holds correspondence information between movable part attitude information and muscle activity information linked to the movable part attitude information, the movable part attitude information indicating an attitude of a movable part of training equipment when an exerciser moves a body of the exerciser along a trajectory defined by the training equipment, the muscle activity information indicating a muscle activity of each of muscle parts of the exerciser, the training equipment being equipment that applies a load to muscles of the exerciser;
a display device configured to display a human body muscle anatomy model of which a corresponding part to each muscle part is colored according to a muscle activity indicated in a current muscle activity information; and
a processor configured to
acquire the movable part attitude information while the exerciser is moving the body along the trajectory,
acquire the current muscle activity information for each of the muscle parts corresponding to the acquired movable part attitude information, from the correspondence information in the muscle activity database, and
output the current muscle activity information for each of the muscle parts.

2. The muscle activity output system according to claim 1, wherein:
the training equipment is a pedal exercise device with which the exerciser performs a pedaling exercise while being in a sitting position; and
the movable part attitude information of the training equipment is crank angle information indicating a crank angle of the pedal exercise device.

3. The muscle activity output system according to claim 2, wherein the correspondence information in the muscle activity database is generated by a simulator calculating a change in muscle activity of each muscle part that occurs with a change in the crank angle using a human body model and an exercise device model.

4. The muscle activity output system according to claim 1, wherein:
the muscle activity database holds the correspondence information in such a manner that the correspondence information is linked to exercise condition information indicating an exercise condition of the exerciser; and
the processor is configured to
acquire the exercise condition information, and
acquire the current muscle activity information for each of the muscle parts from the correspondence information corresponding to the acquired exercise condition information.

5. The muscle activity output system according to claim 1, wherein:
the muscle activity database holds the correspondence information in such a manner that the correspondence information is linked to body-specific information of the exerciser; and
the processor is configured to
acquire the body-specific information, and
acquire the current muscle activity information for each of the muscle parts from the correspondence information corresponding to the acquired body-specific information.

6. The muscle activity output system according to claim 1, wherein the muscle activity information indicates muscle activity of deep muscles of the exerciser.

* * * * *